United States Patent
Bakker et al.

(10) Patent No.: US 8,355,131 B2
(45) Date of Patent: Jan. 15, 2013

(54) DEVICE AND METHOD FOR ACQUIRING IMAGE DATA FROM A TURBID MEDIUM

(75) Inventors: Levinus Pieter Bakker, Eindhoven (NL); Martinus Bernardus Van Der Mark, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 582 days.

(21) Appl. No.: 12/525,748

(22) PCT Filed: Jan. 29, 2008

(86) PCT No.: PCT/IB2008/050308
§ 371 (c)(1),
(2), (4) Date: Aug. 4, 2009

(87) PCT Pub. No.: WO2008/096289
PCT Pub. Date: Aug. 14, 2008

(65) Prior Publication Data
US 2010/0027018 A1    Feb. 4, 2010

(30) Foreign Application Priority Data
Feb. 5, 2007    (EP) ..................................... 07101710

(51) Int. Cl.
*G01N 21/55* (2006.01)
*G01N 21/00* (2006.01)
*A61B 5/00* (2006.01)
*A61B 6/00* (2006.01)

(52) U.S. Cl. ........ 356/436; 356/432; 600/310; 600/473; 600/476

(58) Field of Classification Search .................... None
See application file for complete search history.

(56) References Cited

U.S. PATENT DOCUMENTS

| | | | |
|---|---|---|---|
| 4,384,336 A * | 5/1983 | Frankle et al. ................ 382/302 |
| 4,495,949 A | 1/1985 | Stoller | |
| 5,907,406 A | 5/1999 | Papaioannou et al. | |
| 5,907,593 A * | 5/1999 | Hsieh et al. ....................... 378/4 |
| 6,230,045 B1 * | 5/2001 | Hoogenraad et al. ......... 600/473 |
| 6,240,309 B1 | 5/2001 | Yamashita et al. | |
| 6,681,130 B2 * | 1/2004 | Wake et al. ................... 600/407 |
| 6,687,532 B2 | 2/2004 | Ohmae et al. | |
| 7,006,592 B2 * | 2/2006 | Ali et al. ........................... 378/4 |
| 7,006,676 B1 * | 2/2006 | Zeylikovich et al. ......... 382/131 |
| 7,054,002 B1 * | 5/2006 | Sevick-Muraca et al. .... 356/317 |
| 7,898,649 B2 * | 3/2011 | Masumura ...................... 356/73 |
| 2005/0047546 A1 | 3/2005 | Fox et al. | |
| 2008/0309940 A1 * | 12/2008 | Van Der Mark et al. ..... 356/435 |
| 2009/0069695 A1 * | 3/2009 | Nielsen et al. ................ 600/473 |
| 2009/0264772 A1 * | 10/2009 | Van Der Brug et al. ...... 600/476 |
| 2010/0272331 A1 * | 10/2010 | Brendel et al. ................ 382/128 |

FOREIGN PATENT DOCUMENTS

| | | |
|---|---|---|
| DE | 4309531 A1 | 9/1994 |
| WO | 0153802 A2 | 7/2001 |
| WO | 0241760 A2 | 5/2002 |
| WO | 03008945 A1 | 1/2003 |

\* cited by examiner

*Primary Examiner* — Gordon Stock, Jr.

(57) ABSTRACT

A device and method of acquiring image data from a turbid medium using a diffuse optical tomography device including irradiating the turbid medium at a plurality of first spatial positions, collecting light emanating from the turbid medium at a plurality of second spatial positions, splitting the light collected from each second spatial position into at least two optical channels, measuring the intensity of the split light in each optical channel of the at least two optical channels using photo detectors, and reconstructing an image of the turbid medium from the measured intensities.

17 Claims, 3 Drawing Sheets

DEVICE AND METHOD FOR ACQUIRING IMAGE DATA FROM A TURBID MEDIUM

TECHNICAL FIELD

The invention relates to a device for imaging a turbid medium, as well as a method of acquiring image data from a turbid medium and a computer program product comprising computer executable instructions for acquiring image data from a turbid medium.

BACKGROUND AND RELATED ART

X-ray computer tomography, ultrasonic computer tomography and MRI are well known methods for localizing objects in a turbid medium, especially for the localization of breast cancer and tumors. Optical computer tomography uses the fact, that near infrared light exhibits a high transmissivity with respect to biological tissues and growth of tumors or cancer can be monitored by a characteristic absorption of light in breast tissue. An advantage for using an optical computer tomography device is also, that special contrast agents with fluorescent tags can be used, in order to localize cancer areas in breast tissue. The fluorescent contrast agent is thereby adapted to accumulate in the cancer area. Consequently, the cancer area labeled with the contrast agent emanates a characteristic fluorescing light upon irradiation with a laser at a certain wavelength or upon irradiation with a light source of certain bandwidth.

Typical devices for localizing an object in a turbid medium can be seen in U.S. Pat. No. 6,687,532 B2. A common disadvantage using an optical computer tomography apparatus is, that the dynamic range of the intensity of the light emanating from the irradiated turbid medium is rather large. Therefore, respective photo detectors have to cover a large dynamic sensitivity range. This necessitates complex and rather expensive electronics. Furthermore, for diffuse optical fluorescence measurements, the optical fluorescence signal from the turbid medium is typically very small and an up to 100 times larger transmission contribution has to be measured at the same time together with the small fluorescent signal. This again necessitates complex and expensive optics with large dynamic range photo detectors of precisely defined spectral range.

SUMMARY OF THE INVENTION

The present invention provides a method of acquiring image data from a turbid medium using a diffuse optical tomography device. The method comprises irradiating the turbid medium at a plurality of first spatial positions and collecting light emanating from the turbid medium at a plurality of second spatial positions. The light collected from each second spatial position is split into at least two optical channels and the intensity of the split light in each optical channel of the at least two optical channels is measured using photo detectors. Finally, an image of the turbid medium is reconstructed from the measured intensities. Any systematic errors have to be cancelled by for example a proper calibration procedure.

This method of splitting the light collected from each second spatial position into two or more optical channels has the advantage, that in each optical channel respective photo detectors can be used which are adapted for special measurements regarding for example specific dynamic optical ranges or specific spectral ranges.

In accordance with an embodiment of the invention, the turbid medium is irradiated at a plurality of different wavelengths. This allows to obtain optimal contrast of a reconstructed image for different optical characteristics of the turbid medium.

In accordance with an embodiment of the invention, the measurement of the intensity of the split light is performed with different photo detector sensitivities for each channel within the at least two optical channels. This allows to use less complex and inexpensive electronics, since the dynamic sensitivity ranges of the individual photo detectors can be lower.

In accordance with an embodiment of the invention, the measurement of the intensity of the split light is performed at different wavelengths for individual channels of the at least two optical channels. This has the advantage, that for example in fluorescence measurements, the optical signal originating from the fluorescence contribution and the much larger transmission contribution can be measured at the same time, even though the fluorescence contribution is approximately two orders of magnitude lower than the transmission contribution. This embodiment not only decreases the necessary dynamic sensitivity range of the detectors, it also speeds up the measurements and decreases systematic errors originating from fluid instability, patient motion artifacts and laser power fluctuations, since fluorescence and transmission contributions are both measured at the same time at the same position.

It is important to note, that for the image reconstruction, both the fluorescence and the transmission signal are used. In order to further improve for example measurements of fluorescence and transmission signal contributions, the measurement of the intensity of the split light is performed using different optical filters for each channel of the at least two optical channels.

In accordance with an embodiment of the invention, at least one optical channel of the at least two optical channels is selected for the image reconstruction according to a measure of quality of the measured intensity of the split light in the respective at least two optical channels. This has the advantage, that for example different photo detectors with different spectral and/or dynamical sensitivity properties can be used for a simultaneous measurement in all optical channels, whereas for the image reconstruction only signals from the most suitable adapted photo detectors are selected and used.

This can for example be applied for photo detectors with cascaded dynamical sensitivities, wherein in an embodiment of the invention the light intensity saturation of the photo detectors is measured in each optical channel of the at least two optical channels, wherein only optical channels with respective non-saturated photo detectors are selected for usage for the image reconstruction.

In another aspect the invention relates to a diffuse optical tomography device for acquiring image data from a turbid medium, comprising a light source for irradiating the turbid medium at a plurality of first spatial positions, collectors for collecting light emanating from the turbid medium at a plurality of second spatial positions, means for splitting the at each second spatial position collected light into at least two optical channels, a photo detector for measuring the intensity of the split light in each optical channel of the at least two optical channels and a data processing system for reconstructing an image of the turbid medium from the measured intensities.

In accordance with an embodiment of the invention, the means for splitting the detected light are adapted as fiber Y-couplers and/or semi-transparent mirrors. This allows the usage of standard optical components, which reduces maintenance and construction costs of the optical tomography device.

In accordance with an embodiment of the invention, the diffuse optical tomography device further comprises means adapted for a quality monitoring of measured intensities of optical signals in each of the optical channels. Thereby, preferably the data processing system is adapted to perform the monitoring of the quality of the measured intensities of the optical signals.

In accordance with an embodiment of the invention, within the at least two optical channels, the respective photo detectors for measuring the intensity of the optical signals are adapted for detecting light with different light intensity sensitivity and/or different light wavelength sensitivity.

In accordance with an embodiment of the invention, within the at least two optical channels the sensitivity ranges of the photo detectors are overlapping. By using overlapping sensitivity ranges of the photo detectors, an optimum coverage of all dynamic ranges of the intensities of the light emanating from the turbid medium can be achieved.

In accordance with an embodiment of the invention, the diffuse optical tomography device further comprises a filter for an optical channel. The filter can for example be adapted for blocking of turbid medium transmission light and transmitting turbid medium fluorescence light. This has the advantage, that photo detectors with respective highly adapted spectral and dynamic ranges for the turbid medium transmission and fluorescence light measurements can be used effectively. Rather expensive and complex optics comprising large dynamic range detectors can be avoided.

In accordance with an embodiment of the invention, the diffuse optical tomography device further comprises a selection unit, the selection unit being adapted for selection of an optical channel.

In another aspect, the invention relates to a computer program product comprising computer executable instructions for controlling a light irradiation of a turbid medium at a plurality of first spatial positions in a diffuse optical tomography device, as well as controlling a selection unit. Thereby, the selection unit is adapted for a selection of the photo detector, the photo detector is connected to an optical channel of at least two optical channels, the at least two optical channels are connected to means for splitting light and the light is collected at each of second spatial positions in a diffuse optical tomography device. The computer program product further comprises computer executable instructions for reconstructing an image of the turbid medium from measured signal intensities, whereby the signal intensities are originating from the selected photo detectors.

The reconstruction may be performed by a reconstruction software that operates independently of the splitting of light per spatial detection position.

The reconstruction may be upgraded to account for the signal levels detected at the respective optical channels; e.g. to account for differences in transmission of the respective channels.

BRIEF DESCRIPTION OF THE DRAWINGS

In the following preferred embodiments of the invention are described in greater detail by way of example only by making reference to the drawings in which.

DETAILED DESCRIPTION

Figure 1:
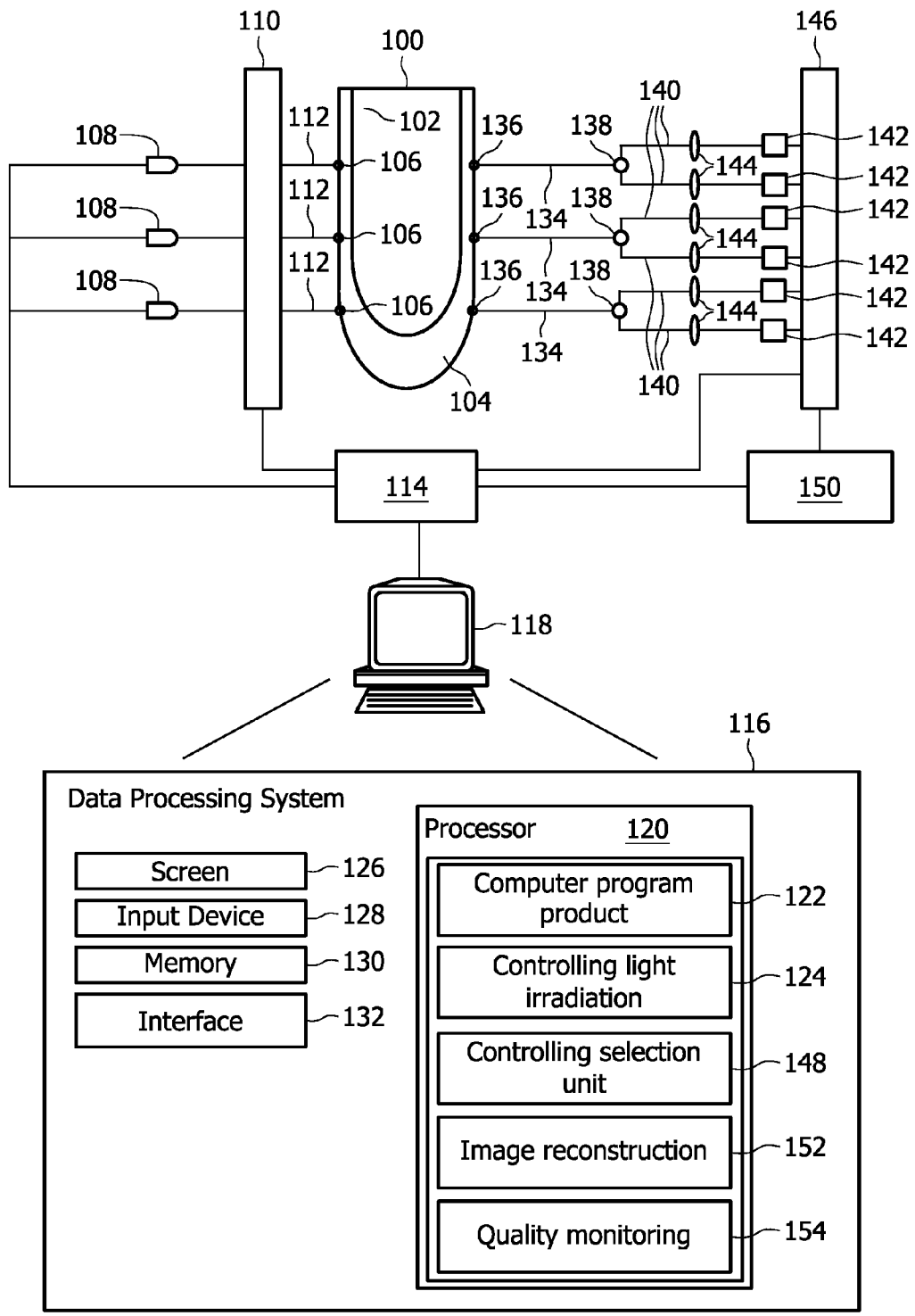
FIG. 1 is a block diagram of an embodiment of a diffuse optical tomography device.

FIG. 1 is a block diagram of an embodiment of a diffuse optical tomography device. The diffuse optical tomography device comprises a holder 100 being adapted for receiving a turbid medium 102, the turbid medium 102 being immersed in a calibration medium 104. The calibration medium 104 corresponds to a scattering fluid, which scattering properties closely match the scattering properties of the turbid medium 102.

The turbid medium 102 is irradiated at a plurality of first spatial positions 106 using light sources 108. The light sources 108 are preferably adapted as for example different lasers, each laser emanating light at a different wavelength, for example 680 nm, 780 nm, 870 nm. The light sources 108 are connected to a multiple optical switch 110. The multiple optical switch 110 connects the light sources 108 to a large number of fibers 112, typically in between 100 to 500 fibers 112. Each fiber 112 is connected to the holder 100 at the plurality of first spatial positions 106. In this way, each one of the optical fibers 112 can provide light in the holder.

By appropriately switching the multiple optical switch 110, all the optical fibers 112 will emit light subsequently. Thereby, the light sources 108 and the multiple optical switch 110 are controlled by a control device 114. The control device 114 is connected to a data processing system 116.

The data processing system 116 may be implemented as a computer system 118 comprising at least one computer or a network of computers. The data processing system 116 comprises a processor 120 suitable for execution of a computer program product 122. The computer program product 122 comprises computer executable instructions comprising for example instructions 124 for controlling the light irradiation of the turbid medium 102 at the plurality of first spatial positions 106 in the diffuse optical tomography device.

To provide interaction with a user, embodiments of the invention can be implemented on the data processing system 116 having a display device 126 such as a CRT (Cathode Ray Tube) or LCD (Liquid Crystal Display) monitor for displaying information to the user and input devices 128 like a keyboard and a pointing device such as a mouse or a trackball by which the user can provide input to the computer.

The data processing system 116 further comprises a memory 130. The memory 130 may comprise mass storage devices for storing data as well as any storage device suitable for embodying computer program instructions and data including all forms of non-volatile memory, including by way of example semi-conductor memory devices such as EPROM, EEPROM and flash memory devices, magnetic discs such as internal hard discs, removable discs, CD-ROM and DVD-ROM discs.

In order to provide communication between the data processing system 116 and the optical hardware of the optical tomography device, an interface 132 is adapted for communication with the control device 114.

The light emanating from the optical fibers 112 is scattered by the scattering fluid 104 and the turbid medium 102 and is collected by for example optical fibers 134 at a plurality of second spatial positions 136. Thereby, typically in between 100 to 500 optical fibers 134 are used for the light collection. At each second spatial position 136 the collected light is split into at least two optical channels 140 using for example fiber Y-couplers and/or semi-transparent mirrors 138. Each optical channel 140 of the at least two optical channels is adapted as an optical fiber. A photo detector 142 is used for measuring the intensity of the split light in each respective optical channel 140.

Within each set of split optical channels 140, the respective photo detectors 142 for measuring the intensity of the optical signals are adapted for detecting light with different light intensity sensitivity and/or different light wavelength sensitivity. Preferably the sensitivity ranges of the photo detectors 142 are overlapping.

In order to for example block turbid medium transmission light and transmit turbid medium fluorescence light, the optical channels 140 may further comprise filters 144 being adapted for transmitting or blocking light of a certain given spectral range.

The diffuse optical tomography device further comprises a selection unit 146, the selection unit 146 being adapted for selection of an optical channel 140. The selection unit 146 is controlled with means of the interface 114 by the data processing system 116 using computer executable instructions 148. The data processing system 116 is adapted to perform a monitoring of the quality of the measured intensity of the optical signal in each of the optical channels 140 using computer executable instructions 154.

At least one optical channel of the at least two optical channels 140 is selected according to a measure of quality of the measured intensity of the split light in the respective at least two optical channels 140. For example the light intensity saturation of the photo detectors 142 is measured in each optical channel of the at least two optical channels 140 and only optical channels with respective non-saturated photo detectors are selected for usage for the image reconstruction by the data processing system 116.

The selection unit 146 selects the appropriate photo detectors 142 and an analogue digital converter 150 connected to the interface 114 converts the analogue signals from the selected photo detectors 142 into digital signals. The digitized signals are transferred to the data processing system 116 with means of the control device 114.

In an alternative embodiment, all analogue signals from all photo detectors 142 are first converted into digital signals using the analogue digital converter 150. After conversion, the selection unit 146 being controlled with means of the interface 114 is used for selection of the respective digitized optical signals. Thereby, the data processing system 116 is adapted to perform the monitoring of the quality of the measured intensity of the digitized optical signals using computer executable instructions 154.

Generally, the selection unit 146 and/or the interface 114 and/or the analogue digital converter 150 can be adapted as separate devices or can be integrated into the computer system 118.

An image of the turbid medium is reconstructed by the data processing system 116 from the respective signal intensities originating from the selected photo detectors 142 using computer executable instructions 152.

Figure 2:
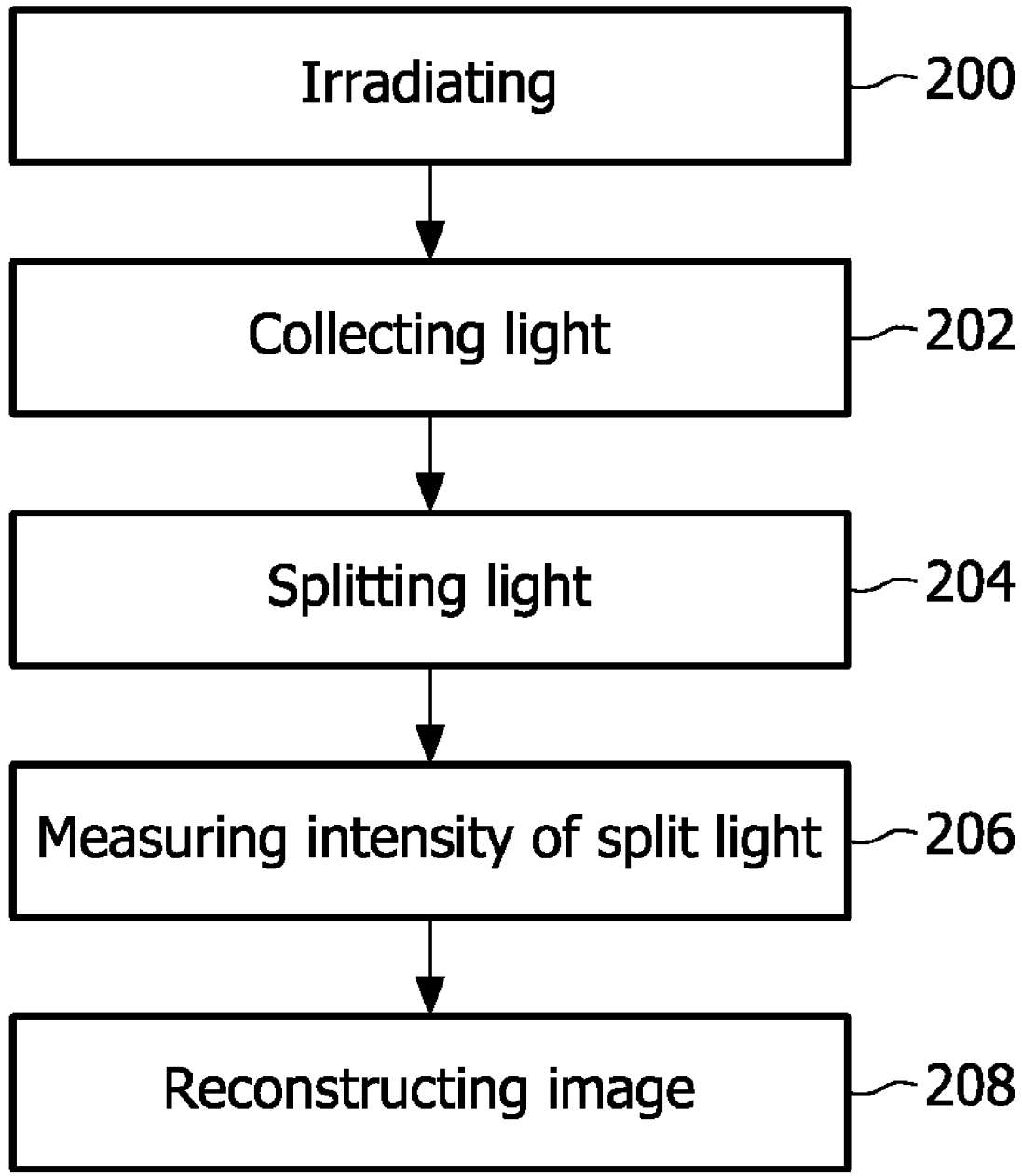
FIG. 2 shows a flowchart illustrating a method of acquiring image data from a turbid medium using a diffuse optical tomography device.

FIG. 2 shows a flowchart illustrating a method of acquiring image data from a turbid medium using a diffuse optical tomography device. In step 200 the turbid medium is irradiated at a plurality of first spatial positions. Light emanating from the turbid medium is collected in step 202 at a plurality of second spatial positions. The light collected from each second spatial position is split in step 204 into at least two optical channels.

For example, a suitable embodiment could be a two channel system having 99% of the light at a given second spatial position in a first channel and 1% of the light in a second channel. A photo detector connected to the first channel can be used for detecting light with low intensities and/or the detector connected to the second channel can be used for detecting light with high intensities.

A variation of this embodiment could be for example a three channel system, where the light is split into three components with respective first, second and third channels with 98%, 1% and 1% transmission. Thereby, photo detectors connected to the channels can be adapted to be sensitive to certain different wavelengths of the split light. This is especially important for combined fluorescent and transmission light measurements.

Regarding only two optical channels, the intensity of the split light is measured in each optical channel of the at least two optical channels in step 206 using photo detectors. Finally in step 208, an image of the turbid medium is reconstructed from the measured intensities.

Figure 3:
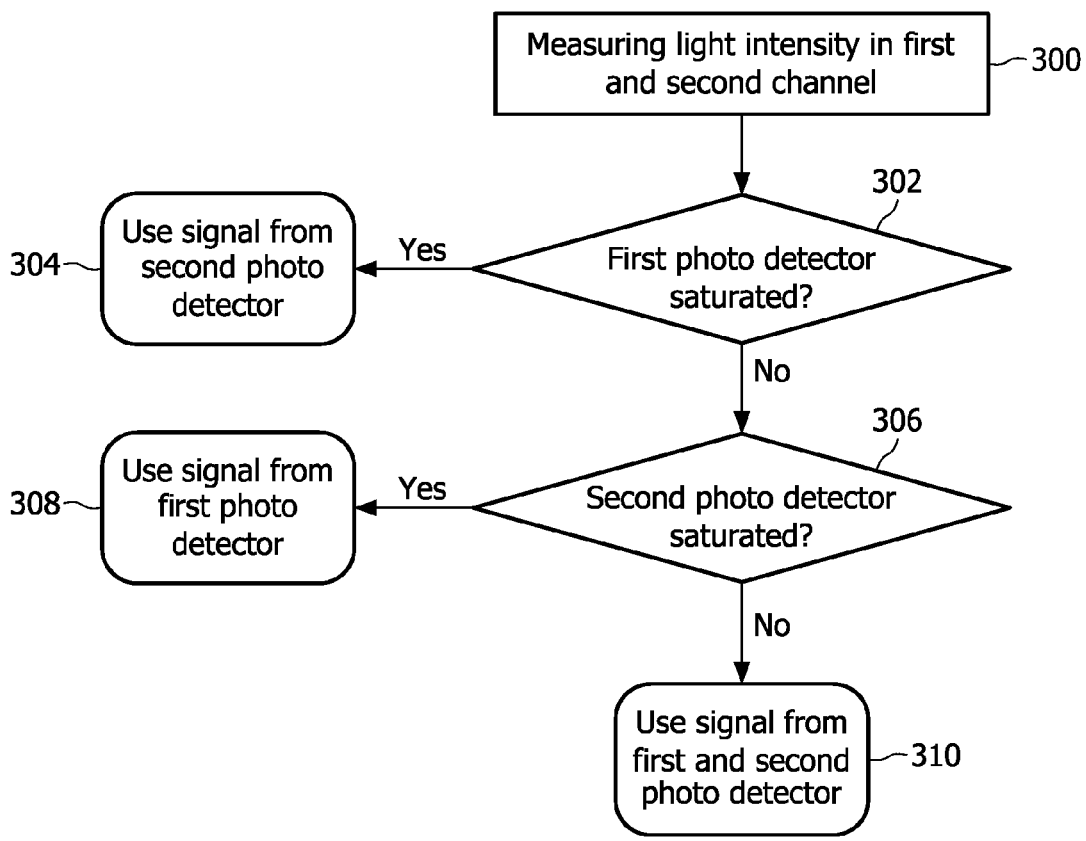
FIG. 3 shows a flowchart illustrating a method of selecting photo detectors according to a respective light intensity saturation of photo detectors for acquiring image data from a turbid medium.

FIG. 3 shows a flowchart illustrating a method of selecting photo detectors according to a respective light intensity saturation of photo detectors for acquiring image data from a turbid medium. While irradiating the turbid medium at a plurality of first spatial positions, light emanating from the turbid medium is collected at a plurality of second spatial positions. The light collected from a given second spatial position is split into a first and a second optical channel. In step 300 the intensity of the split light in the first and second optical channel is measured using photo detectors. In step 302 light intensity saturation of the first photo detector is measured and analyzed by for example a data processing system. In case the first photo detector is saturated, in step 304 only the signal from the second photo detector is used for an image reconstruction. If step 302 returns, that the first photo detector is not saturated, for example the data processing system determines in step 306, whether the second photo detector is saturated. In case step 306 returns, that the second photo detector is saturated, only the signal from the first photo detector is used in step 308 for reconstructing an image of the turbid medium from the measured intensity. If step 306 returns, that the second photo detector is also not saturated, in step 310 both signals from the first and second photo detector are used for the image reconstruction.

One of the photo detectors is considered to be in saturation if it reaches its maximum output signal level. For example, if the output range is from 0V to 10V, the respective photo detector is considered to be in saturation if it provides an output signal of 10V.

In case the first and the second photo detectors are both saturated, the data processing system can either discard the respective measurement point or in an alternative for example turn down the laser power used to irradiate the turbid medium. In a further alternative, respective light attenuators located in the light path of the photo detectors can be switched in order to reduce the light intensity of the split light.

It has to be noted, that the flowchart in the FIG. 3 illustrates an exemplary method of selecting respective photo detectors connected to only two optical channels. However, for practically applied image reconstruction, a large multitude of non-saturated photo detectors is required. The image reconstruction is always based on a combined measurement of light intensities in a large multitude of non-saturated photo detectors.

List of Reference Numerals

| | |
|---|---|
| 100 | Holder |
| 102 | Turbid medium |
| 104 | Calibration medium |
| 106 | First spatial position |
| 108 | Light source |
| 110 | Multiple optical switch |
| 112 | Optical fiber |
| 114 | Control device |
| 116 | Data processing system |
| 118 | Computer system |
| 120 | Processor |
| 122 | Computer program product |
| 124 | Instruction |
| 126 | Display |
| 128 | Input device |
| 130 | Memory |
| 132 | Interface |
| 134 | Optical fiber |
| 136 | Second spatial position |
| 138 | Y-coupler |
| 140 | Optical fiber |
| 142 | Photo detector |
| 144 | Filter |
| 146 | Selection unit |
| 148 | Instruction |
| 150 | A/D converter |
| 152 | Instructions |
| 154 | Instructions |

The invention claimed is:

1. A method of acquiring image data from a turbid medium using a diffuse optical tomography device, the method comprising acts of:
    irradiating the turbid medium simultaneously at a plurality of first spatial positions,
    collecting light emanating from the turbid medium simultaneously at a plurality of second spatial positions,
    splitting the light collected at each second spatial position into at least two optical channels,
    measuring an intensity of the split light simultaneously in each individual optical channel of the at least two optical channels using a corresponding photo detector for each individual optical channel,
    reconstructing an image of the turbid medium from either selected one of the at least two optical channels.

2. The method of claim 1, wherein the turbid medium is irradiated at a plurality of different wavelengths.

3. The method of claim 1, wherein the measurement of the intensity of the split light is performed with different photo detector sensitivities for individual channels of the two optical channels.

4. The method of claim 1, wherein the measurement of the intensity of the split light is performed at different wavelengths for individual channels of the at least two optical channels.

5. The method of claim 1, wherein the measurement of the intensity of the split light is performed using different optical filters for individual channels of the at least two optical channels.

6. The method of claim 1, comprising an act of selecting at least one optical channel of the at least two optical channels according to a measure of quality of the measured intensity of the split light in the respective at least two optical channels.

7. The method of claim 1, wherein light intensity saturation of the photo detectors is measured in each optical channel of the at least two optical channels, wherein only optical channels with respective non-saturated photo detectors are selected for usage for the image reconstruction.

8. A diffuse optical tomography device for acquiring image data from a turbid medium comprising:
    a light source for irradiating the turbid medium simultaneously at plurality of first spatial positions,
    collectors for collecting light emanating from the turbid medium simultaneously at a plurality of second spatial positions,
    splitters for splitting the collected light at each second spatial position into at least two optical channels,
    a corresponding photo detector for measuring an intensity of the split light in the individual corresponding optical channels of the at least two optical channels,
    a data processing system for reconstructing an image of the turbid medium from either selected one of the at least two optical channels.

9. The diffuse optical tomography device of claim 8, further comprising an optical filter and/or optical lenses for at least one of the optical channels.

10. The diffuse optical tomography device of claim 8, wherein the splitters are fiber Y-couplers and/or semi-transparent mirrors.

11. The diffuse optical tomography device of claim 9, wherein the filter is adapted for blocking of turbid medium transmission light and transmitting turbid medium fluorescence light.

12. The diffuse optical tomography device of claim 10, further comprising a selection unit, the selection unit being adapted for selection of one of the at least two optical channels.

13. The diffuse optical tomography device of claim 10, further comprising a processor for monitoring a quality of the measured intensity of the optical signal in each of the optical channels.

14. The diffuse optical tomography device of claim 10, wherein within the at least two optical channels the respective photo detectors for measuring the intensity of the optical signals are adapted for detecting light with different light intensity sensitivity and/or different light wavelength sensitivity.

15. The diffuse optical tomography device of claim 13, wherein the data processing system is adapted perform the monitoring of the quality of the measured intensity of the optical signal.

16. The diffuse optical tomography device of claim 14, wherein within the at least two optical channels sensitivity ranges of the photo detectors are only partially overlapping.

17. A non-transitory computer program storage product containing computer executable instructions for acquiring image data from a turbid medium, wherein execution of the computer executable instructions by a processor causes the processor to carry out acts of:
    controlling a light irradiation of a turbid medium simultaneously at a plurality of first spatial positions in a diffuse optical tomography device,
    measuring an intensity of the split light simultaneously at a plurality of second spatial positions in each individual optical channel of at least two optical channels using a corresponding photo detector for each individual optical channel,
    controlling a selection unit to select a photo detector from a plurality of photo detectors, each one of the photo detectors being connected to an optical channel of the at least two optical channels, the at least two optical channels being connected to a splitter for splitting light, the light being collected simultaneously at each of the second spatial positions in the diffuse optical tomography device, and
    reconstructing an image of the turbid medium from either selected photo detector of the at least two optical channels.

* * * * *